United States Patent [19]

McAtee

[11] Patent Number: 4,968,892

[45] Date of Patent: Nov. 6, 1990

[54] FLUORESCENT PENETRANT INSPECTION SENSOR

[75] Inventor: James D. McAtee, Cincinnati, Ohio

[73] Assignee: General Electric Eompany, Cincinnati, Ohio

[21] Appl. No.: 946,267

[22] Filed: Dec. 24, 1986

[51] Int. Cl.$^5$ .................... G01N 21/91; G01N 21/64
[52] U.S. Cl. .................................. 250/458.1; 250/302
[58] Field of Search .................. 250/458.1, 461.1, 302; 356/317, 318, 417

[56] References Cited

U.S. PATENT DOCUMENTS

| | | | |
|---|---|---|---|
| 3,673,417 | 6/1972 | Wahli | 250/227 |
| 3,734,626 | 5/1973 | Roberts et al. | 356/237 |
| 3,999,062 | 12/1976 | Demsky et al. | 250/227 |
| 4,019,060 | 4/1977 | Woodman | 250/458.1 |
| 4,127,773 | 11/1978 | West | 250/461.1 |
| 4,152,723 | 5/1979 | McMahon | 250/363 S |
| 4,536,654 | 8/1985 | Vaerman | 250/302 |
| 4,536,654 | 8/1985 | Vaerman | 250/302 |
| 4,567,370 | 1/1986 | Falls | 250/461.1 |
| 4,577,337 | 3/1986 | Light | 250/302 |
| 4,736,110 | 5/1988 | Awamura | 250/578 |
| 4,758,727 | 7/1988 | Tomei et al. | 250/458.1 |
| 4,816,686 | 3/1989 | Hara et al. | 250/458.1 |

FOREIGN PATENT DOCUMENTS 105464 8/1983 Fed. Rep. of Germany ... 250/458.1

OTHER PUBLICATIONS

Black et al., Scanned-Laser Microscope for Photoluminescence Studies, 7/72 Applied Optics, pp. 1553-1562.

Primary Examiner—Carolyn E. Fields
Attorney, Agent, or Firm—Jerome C. Squillaro

[57] ABSTRACT

A fluorescent penetrant inspection sensor using a laser light source for locating and mapping minute surface flaws. The sensor focuses laser radiation to a point on a surface to be inspected and systematically scans the surface for reflections within a predetermined frequency range. A plurality of lenses on the sensor collect light from fluorescing penetrant. The sensed fluorescence triggers a detector which provides a flaw detection signal and coordinates the signal with the present location of the scanning radiation. Flaws are digitized and mapped for analysis. The sensor includes unique scanning and focusing apparatus with optical systems responsive only to radiation frequencies common to the fluorescent penetrant.

7 Claims, 7 Drawing Sheets

FLUORESCENT PENETRANT INSPECTION SENSOR

FIELD OF THE INVENTION

This invention relates to a method and apparatus for optical inspection of surface defects in a workpiece, and more particularly, to a fluorescent penetrant inspection sensor having a circumferentially arranged lens system for measuring emitted radiation from fluorescent penetrant.

BACKGROUND OF THE INVENTION

The inspection of surfaces of components for turbine engines forms an important part of the overall quality which ensures the reliability of the engine. There are numerous nondestructive evaluation systems which measure surface texture parameters, examine surface defects, and detect surface flaws such as nicks, dents, tears, cracks, etc. These systems transmit some form of energy into or through the workpiece and observe the manner in which the workpiece and energy inter-react. The systems most commonly employed involve ultrasonic magnetic, eddy current or infrared energy. These systems however are not well suited for a workpiece having a large area with a relatively complex configuration such as a jet engine turbine blade.

In these workpieces where the surface are accessible only by the application of a fluorescent penetrant, fluorescent penetrant inspection is well suited to the examination of the workpiece surface. This invention relates to fluorescent penetrant inspection which is used extensively for detection of surface connected discontinuities in relatively complex structural workpieces.

In current fluorescent penetrant inspection practice, an inspector examines a workpiece in which a fluorescent penetrant has been applied to the surface. The penetrant seeps into any surface defects of the workpiece. The workpiece is washed and dryed leaving only penetrant in the defects. The inspector takes the fluorescent penetrant processed workpiece into a darkened room, waits for his eyes to adapt to the darkness and examines the workpiece under ultraviolet light. The ultraviolet light excites the dye in any penetrant in a surface defect causing emission of a visual greenish yellow light. An area emitting this light is typically indicative of a surface defect. The inspector measures the indicated area with a width gauge, or similar device, to assess the size of the area and determine the workpiece's acceptability or rejectability.

One of the problems with this type of inspection is the dependency upon the accuracy of a human inspector to detect a surface defect and to assess the size of the defect. The current manual methods of inspection are labor intensive, slow and subject to human limitations. Because of these problems it is desirable to have a system which is not limited by human response for detecting and measuring surface defects.

SUMMARY OF THE INVENTION

Among the several objects of the present invention may be noted the provision of an improved fluorescent penetrant inspection system and method of operating the system, the provision of such improved system and method in which a sensor automatically scans the exterior surface of the workpiece for determining surface defects or flaws, and the provision of such improved system and method in which the sensor is simple to operate and able to detect very minute surface defects. Another aspect of this invention is the ability of the system to detect surface flaws in a workpiece having a complex configuration surface. These as well as other objects and advantageous features of the present invention will be in part apparent and in part pointed out hereinafter.

In general, a fluorescent penetrant inspection system in one form of the invention has a radiation source for producing a directed beam of exciting or emitting radiation on a location of a surface of a workpiece. A plurality of circumferentially arranged lenses receive emitted radiation from the location and focuses the radiation onto a light receiver. A filter passes primarily only radiation corresponding to emitted radiation from fluorescent penetrant to the light receiver. The light receiver is coupled to a light transmission apparatus which transmits the light to a radiation detector. The radiation detector measures the intensity of the received light at the location on the surface of the workpiece. Movement is effected in the exciting radiation beam and the radiation detector measures emitted radiation versus location on the surface.

In particular, the radiation source comprises a helium cadmium laser beam which is scanned over the exterior surface of the workpiece by a plurality of deflecting mirrors and a focusing lens. The light emissions produced by the excited fluorescent penetrant on a surface defect are collected by a plurality of objective lenses circumferentially arranged around the laser beam. The objective lenses focus the light emission through a plurality of light filters onto a fiber optic transmitting apparatus which transmits the emitted light radiation to a photomultiplier tube. The photomultiplier tube converts the light to electrical signals which are electronically processed for providing flaw indication size and shape information versus location.

BRIEF DESCRIPTION OF THE DRAWINGS

FIGS. 3 and 3A illustrate the sensor's optics;

DETAILED DESCRIPTION OF AN ILLUSTRATIVE EMBODIMENT

With reference to the drawings in general, there is illustrated a fluorescent penetrant inspection sensor 40 and a method in one form of the invention of measuring flaw indications using fluorescent penetrant on the surface of a workpiece 10. It is to be understood that a fluorescent penetrant, such as, for example, RC-77, manufactured by Sherman, Inc. is applied to the surface of the workpiece. The penetrant seeps into defects or flaws such as cracks in the surface of the workpiece. Briefly, and before beginning a detailed description of the invention, exciting radiation such as light having a wavelength for exciting a dye in the penetrant is applied to the surface of the workpiece. The light is focused to a spot size of about four mils. The dye emits light when activated by the source of exciting radiation. The emitted light produced by the excited dye is collected by a plurality of objective lenses 80, filtered and focused on a plurality of light receiving means. The light receiving means are connected to a light transmission means such as a fiber optic bundle (communication link) which transmits the light to a light radiation detector 46, such as a photomultiplier tube. The radiation detector 46 converts the light into electrical signals which are electronically processed to provide light intensity corresponding to location on the surface of the workpiece. The intensity of the light detected varies correspondingly to the amount of dye present on the surface of the workpiece. Since the penetrant containing the dye seeps into a crack, the emitted light intensity is dramatically increased when the radiation source beam is focused on a surface defect containing penetrant. The intensity of this light is measured by the photomultiplier tube to provide flaw indication size and shape information.

Figure 1:
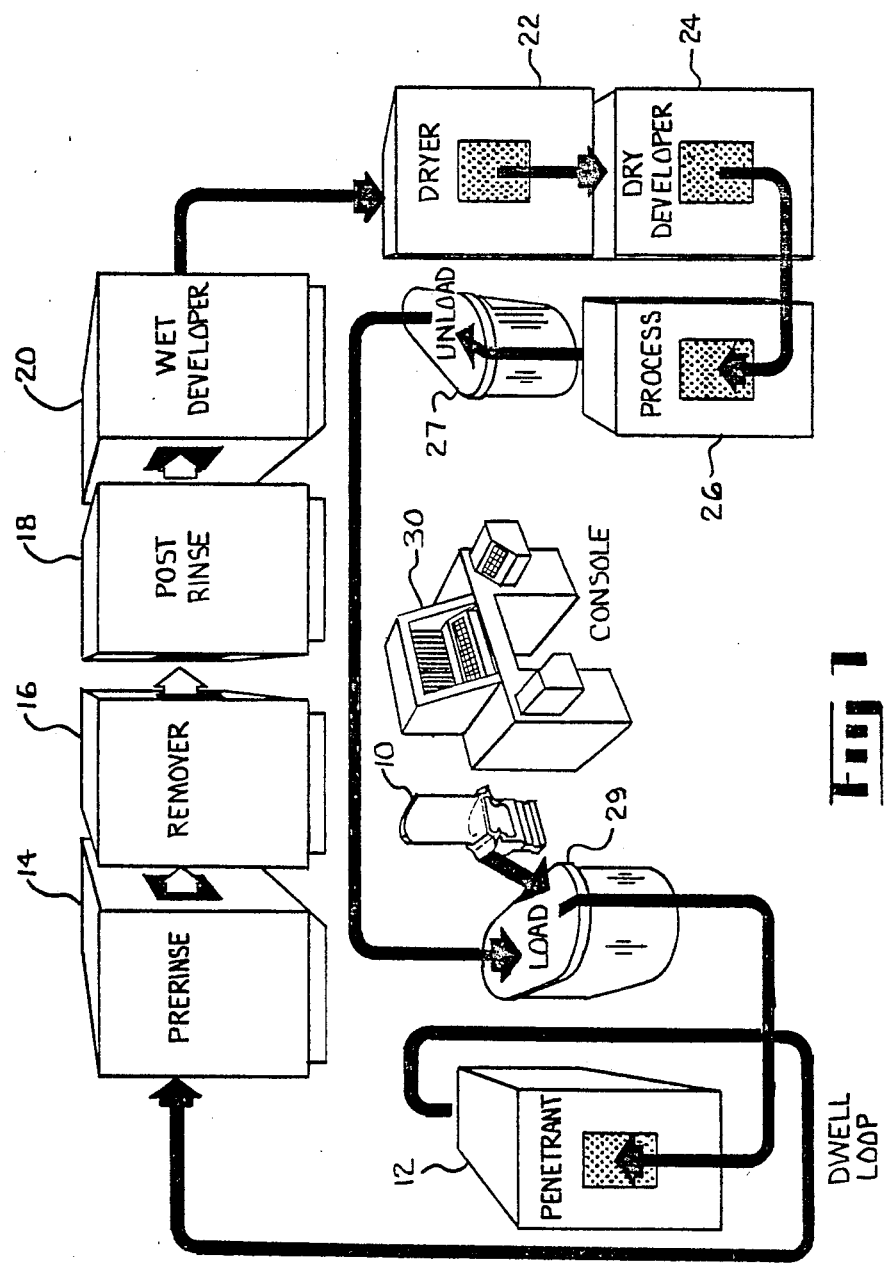
FIG. 1 generally illustrates a method for applying fluorescent penetrant to a workpiece in accordance with the present invention.

Referring to FIG. 1, a functional block diagram illustrates the process of applying a dye penetrant to a workpiece 10 and processing the workpiece through an inspection. Briefly, the workpiece is degreased, cleaned and treated with a fluorescent penetrant containing a fluorescent dye, block 12. The penetrant is then removed from the surface of the part, but remains trapped in flaws such as cracks. The penetrant removal process is illustrated in blocks 14–20. After an appropriate drying time in an oven 22, a thin layer of dry developer is applied to draw the entrapped penetrant to the surface of the workpiece, block 24. The workpiece is then processed by a computer numerical control manipulator and positioned into a beam of exciting radiation, block 26. Both the senser 40 and the workpiece are manipulated such that the radiation beam scans the entire surface of the workpiece. Positioning or manipulating workpieces and scanning apparatus using computer numerical control equipment, such as robots, is well known in the control art and will not be further described. After scanning, the workpiece 10 is unloaded at station 27 and a new workpiece loaded at station 29. Console 30 represents a control station for directing the flow of workpieces and observing the results of the inspection process.

Figure 2:
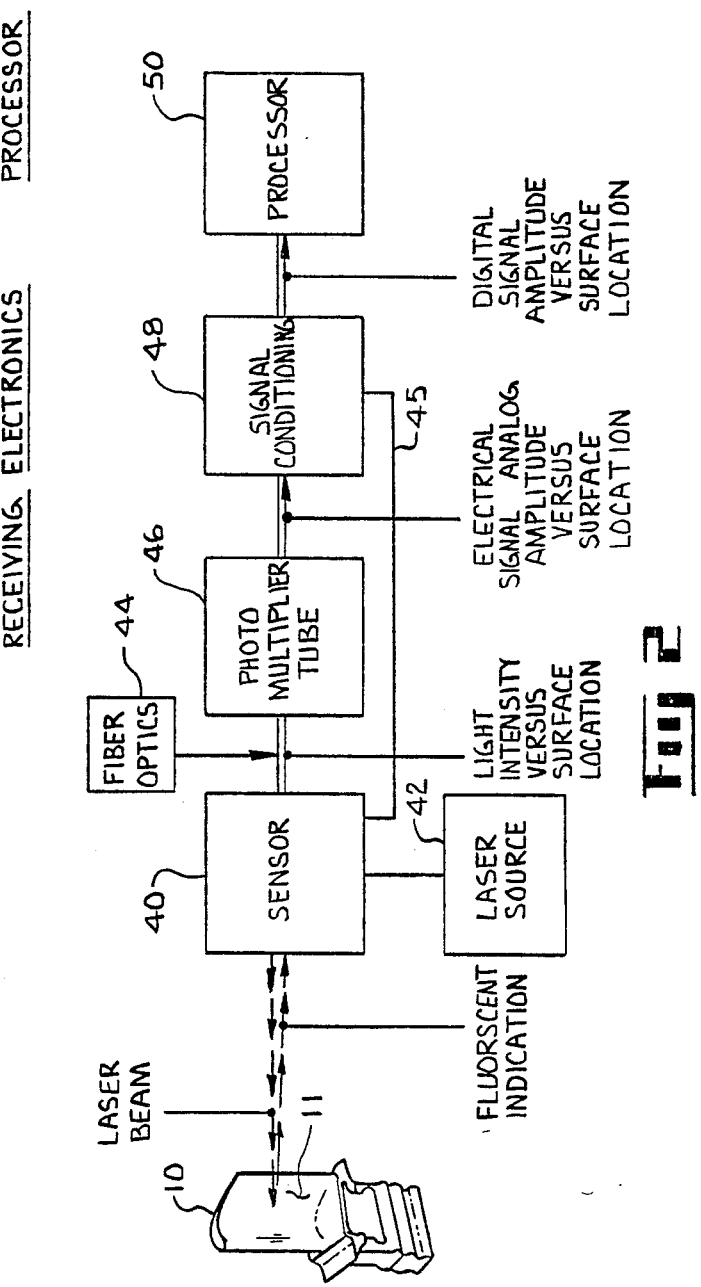
FIG. 2 is a block diagram showing the signal processing operation for the fluorescent penetrant inspection sensor.

FIG. 2 is a block diagram of an illustrative form of signal processing for the inventive fluorescent penetrant inspection system. The sensor 40 includes apparatus for directing an exciting radiation beam from a laser 42 on to a surface 11 of the workpiece 10. The dye trapped in the flaws of the workpiece fluoresces in response to the exciting radiation, and the fluorescence is detected by sensor 40 and transmitted through a fiber optics communication link 44 to a photomultiplier tube 46. The sensor 40 also provides an analog signal via line 45 continuously indicating the precise location of the exciting radiation beam on surface 11. This location signal is applied to an input of a signal conditioner 48. The signal conditioner converts the analog signal to a digital signal and transmits it to a processor 50. The signal conditioner also receives a signal from tube 46 indicative of the emitted radiation from surface 11 due to fluorescing of the entrapped dye. This latter intensity signal is also digitized and transmitted to processor 50. The processor 50 correlates the fluorescence intensity information with the beam location data in order to provide information to console 30 describing the location of surface flaws and their relative size.

Figure 3:
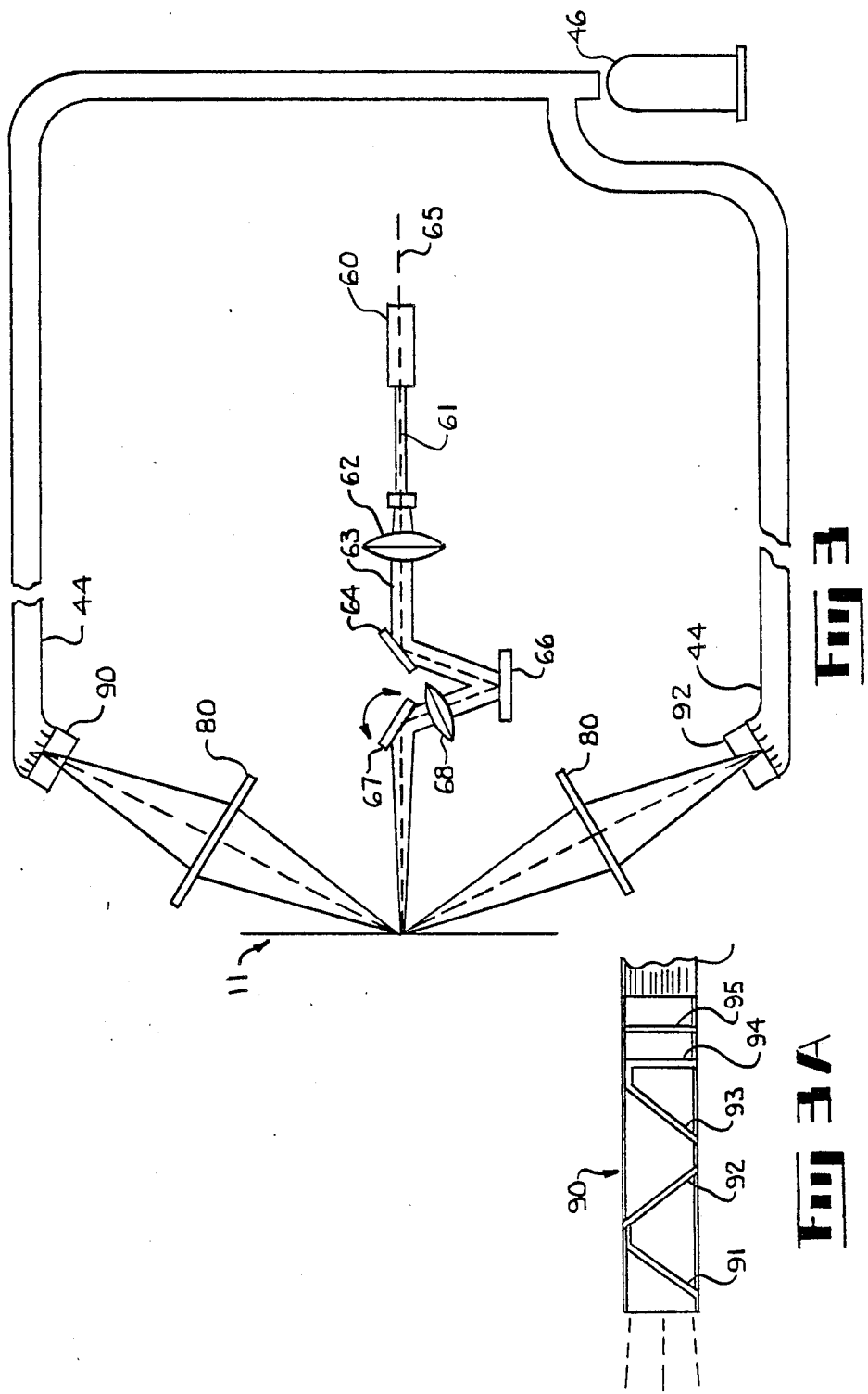

FIG. 3 illustrates a preferred arrangement of optics and optical path for the exciting radiation beam and emitted fluorescence radiation beam. A radiation source in the form of a helium-cadmium laser 60 produces exciting radiation at a primary wavelength of 441.6 nanometers, i.e., essentially a blue colored light beam. In order to focus the laser beam to a small spot it is first expanded by lens 62 and subsequently refocused by lens 68. Located between lenses 62 and 68 are a pair of reflecting mirrors 64, 66 which deflect the beam off its initial axis 65. This deflection allows the beam to approach a plane of surface 11 at a non-perpendicular angle so that a scanning mirror 67 can deflect the beam onto surface 11 in a predetermined pattern. A significant feature of the imaging or scanning optics thus far described is that the initial laser beam 61 is focused to a very small spot size at surface 11. Typically, the beam 61 will have a diameter of 100 to 150 mils. The focused spot on surface 11 optimally has a diameter of 4 to 6 mils. Such a spot size yields better definition, i.e., smaller flaws can be more precisely located and more "samples" per flaw can be obtained.

Continuing with the description of the sensor optics shown in FIG. 3, any light emitted or reflected from surface 11 is focused by a plurality of lenses 80 (best seen in FIG. 7) onto receiving ends of fiber optic communication links 44. Between each of the lenses 80 and the links 44 there is arranged a filter assembly 90 which eliminates any reflected laser light. As mentioned above, the laser 60 produces radiation in the blue light spectrum at 441.6 nanometers. The laser light intensity is such that it would completely swamp fluorescing radiation from the penetrant. More particularly, the penetrant dye has a conversion factor of about two percent and fluoresces at between 520 to 580 nanometers, i.e., in the green-yellow to yellow region. Accordingly, it is necessary to eliminate the overpowering intense reflected blue light using a blue substraction filter 90. The filter 90 (See FIG. 3A) comprises three blue mirrors 91, 92, 93 and two sharp cut-off glass filters 94, 95. Each of the mirrors has a rejection ratio of 10 power. The complete filter 90 has a net rejection ratio of about $10^7$ power which virtually eliminates any blue reflected light while passing the relatively low intensity dye penetrant fluorescence.

The filtered light from filters 90 is coupled through fiber optics links 44 to the photomultiplier tube 46. The tube 46 is of a type well known in the art for converting and amplifying received radiation into a higher intensity signal for conversion to an analog electrical signal. As mentioned above, the analog signal is thereafter converted to a digital signal for processing by processor 50, which processor is typically a digital computer.

The processor 50 receives signals representative of both fluorescence on surface 11 and the position of the exciting radiation spot at the time the dye fluoresces. These two data signals enable the processor to create an image of the surface indicating the location and size of flaws thereon. The radiation spot is scanned over the surface 11 by the oscillatory action of scanning mirror 67. In a preferred embodiment, the mirror 67 is oscillated by a galvanometer type of mechanism so that an electrical signal representative of mirror position is constantly available. In addition to the scanning action of mirror 67, the entire sensor 40 is also physically moved in a direction perpendicular to the scanning direction in order to effect scanning of the entire workpiece surface 11. Signals representative of the position of sensor 40 are also provided to processor 50 to enable construction of the image of the workpiece surface.

Figure 4:
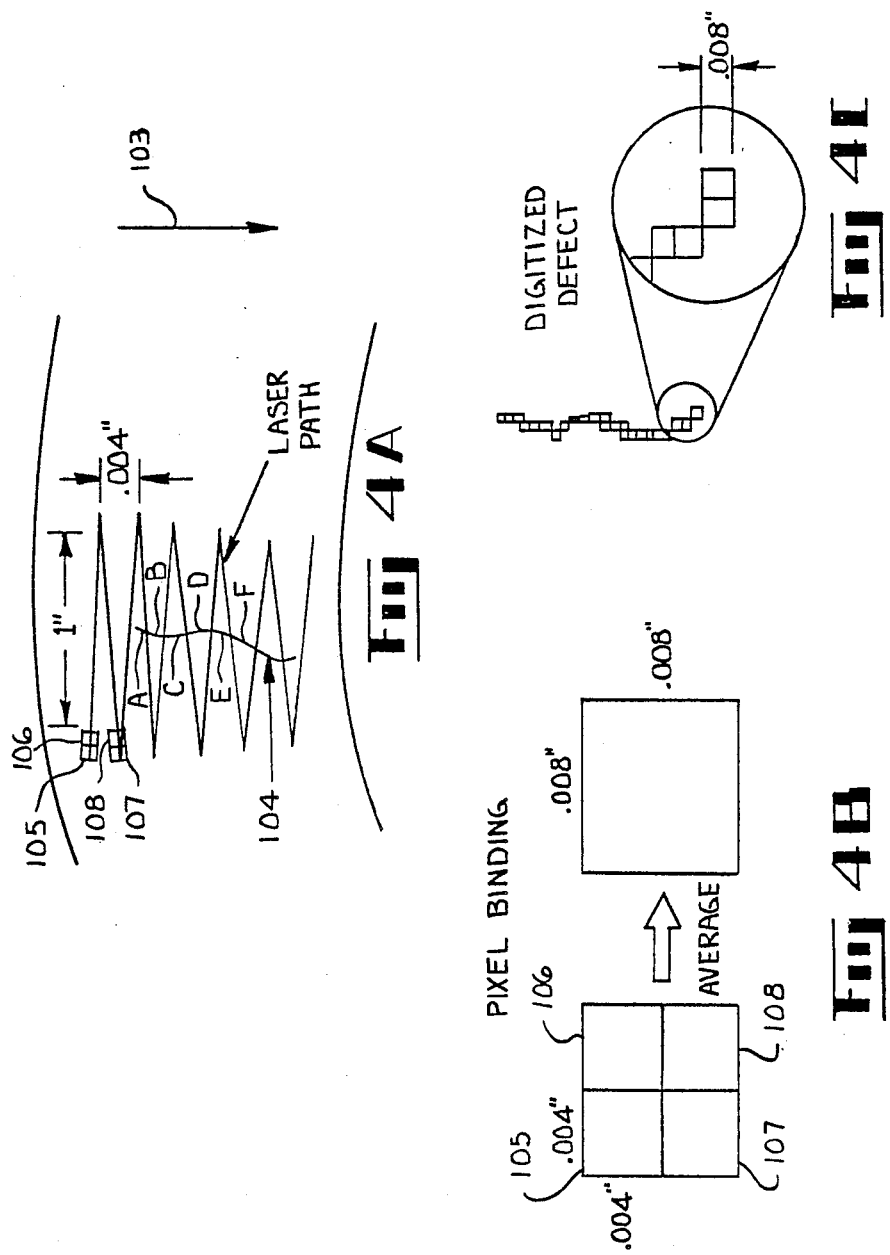
FIGS. 4A–4C illustrate the sensor's geometry.

Referring to FIGS. 4A-C, there is shown the sensor scan geometry as a result of the scanning motion of the oscillatory scanning mirror 67. The scanning mirror 67 causes the radiating laser beam to move in a first direction and then to reverse direction. The sensor 40 is connected to a numerically controlled manipulator which allows the physical movement of the sensor in any of three dimensional directions.

The movement of the beam caused by the scanning mirror 67 coupled with the physical movement of the sensor 40 in the direction as shown by arrow 103 in FIG. 4A, results in a scanning motion as shown in FIG. 4A. The scanning motion causes the radiating beam to intersect a defect, such as crack 104, on several scans. The defect 104 contains penetrant having a fluorescent dye. Each time the beam irradiates the dye, it fluoresces and produces light at a wavelength different from the radiating beam, thus resulting in a measurable signal at the photomultiplier tube. More particularly, as the beam scans the surface 11 of the workpiece it first intersects defect 104 at location A. The laser beam causes light emissions to be produced by the excited dye in defect 104. These light emissions are collected by the plurality of objective lenses 80 and transmitted to the photomultiplier tube 46. The photomultiplier tube 46 generates a signal representative of the intensity of emitted or excited radiation from the dye present in defect 104 at location A. Since the position of the scanning mirror 67 and sensor 40 are known, the location A of the defect 104 is available to the processor 50. As the laser beam continues to scan it will eventually intersect defect 104 in locations B, C, D, E and F causing generation of fluorescing radiation at those locations, which radiation will be detected by tube 46 and result in signals to processor 50.

The velocity at which sensor 40 is moved can be varied to provide more or less coverage or imaging of surface 11. The resolution, i.e., the ability to precisely locate very small flaws, is a function of radiating beam diameter and is preferably focused at between 4–6 mils. For a beam diameter of 4 mils, complete surface coverage occurs if sensor 40 is moved 4 mils for each scan as is shown in FIG. 4A. However, if each 4 mil square area on the workpiece surface is processed, the time required for each workpiece may become excessive. One method of reducing processing time is to average data over multiple 4 mil areas as is shown in FIG. 4B. Such an averaging method also reognizes that false indications of flaws may appear in a single 4 mil area. By averaging, i.e., dividing the net signal by the number of areas, a trigger level can be established to eliminate false indications or noise. Such a technique is particularly useful in examining different types of workpieces such as, for example, steel turbine blades as compared to titanium turbine blades. The steel blades tend to have large flaws while titanium blades have small flaws. Averaging four or more 4 mil areas may be satisfactory for examining steel blades but may result in dismissing flaws in titanium blades. Accordingly, the system is capable of processing areas in smaller combinations such as averaging of two 4 mil areas or actually evaluating each 4 mil area without averaging. An alternate method is to select the two highest reading areas in a group of four or more and average those areas or to select the one highest reading area in a group and evaluate that single area. This alternate method has the advantage of using higher intensity values while still keeping processing time to a reasonable level. FIG. 4C indicates the results of averaging over four areas as shown in FIG. 4B with the digitized plot of defect 104.

Figure 5:
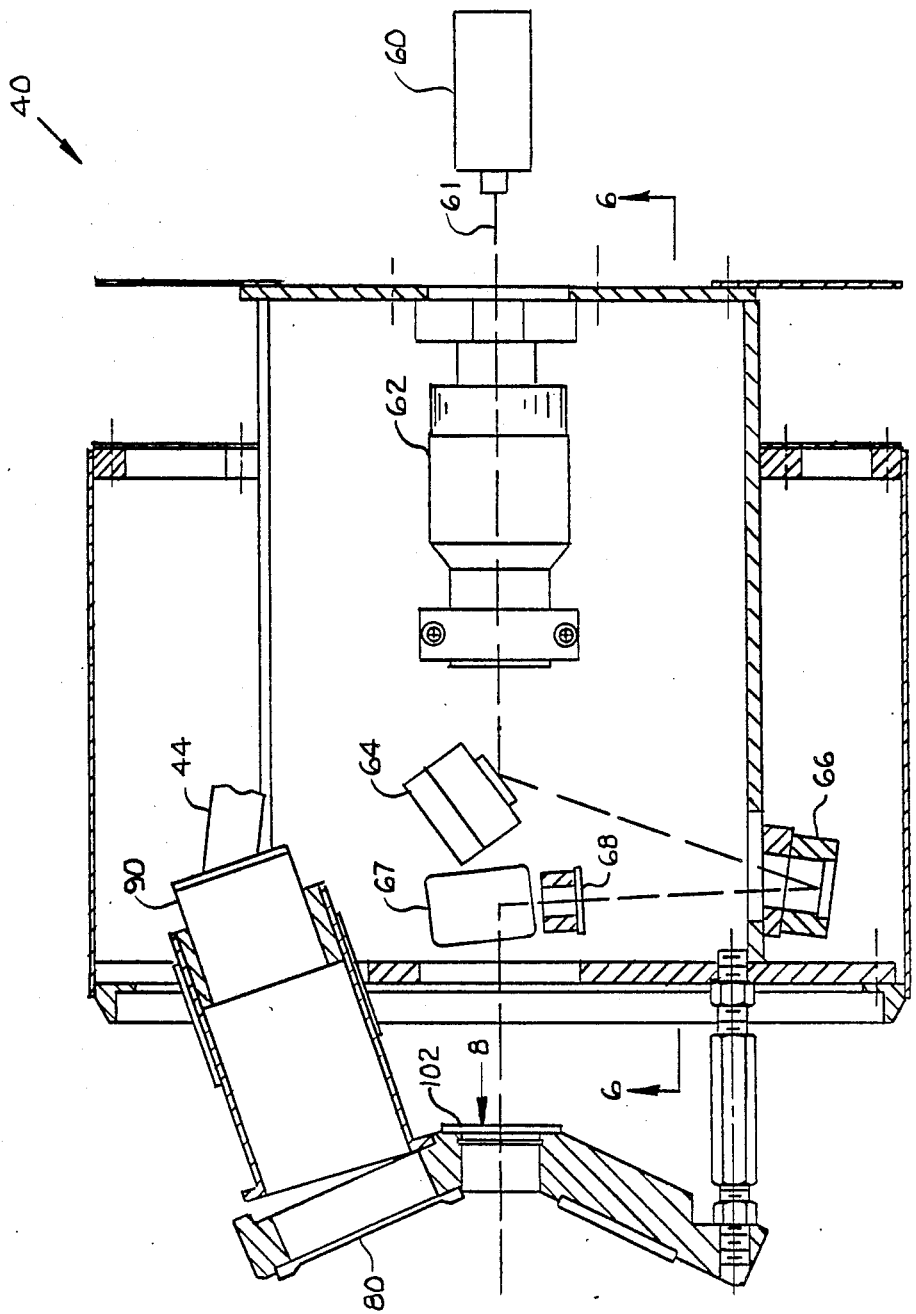
FIG. 5 is a mechanical diagram of the sensor.
Figure 7:
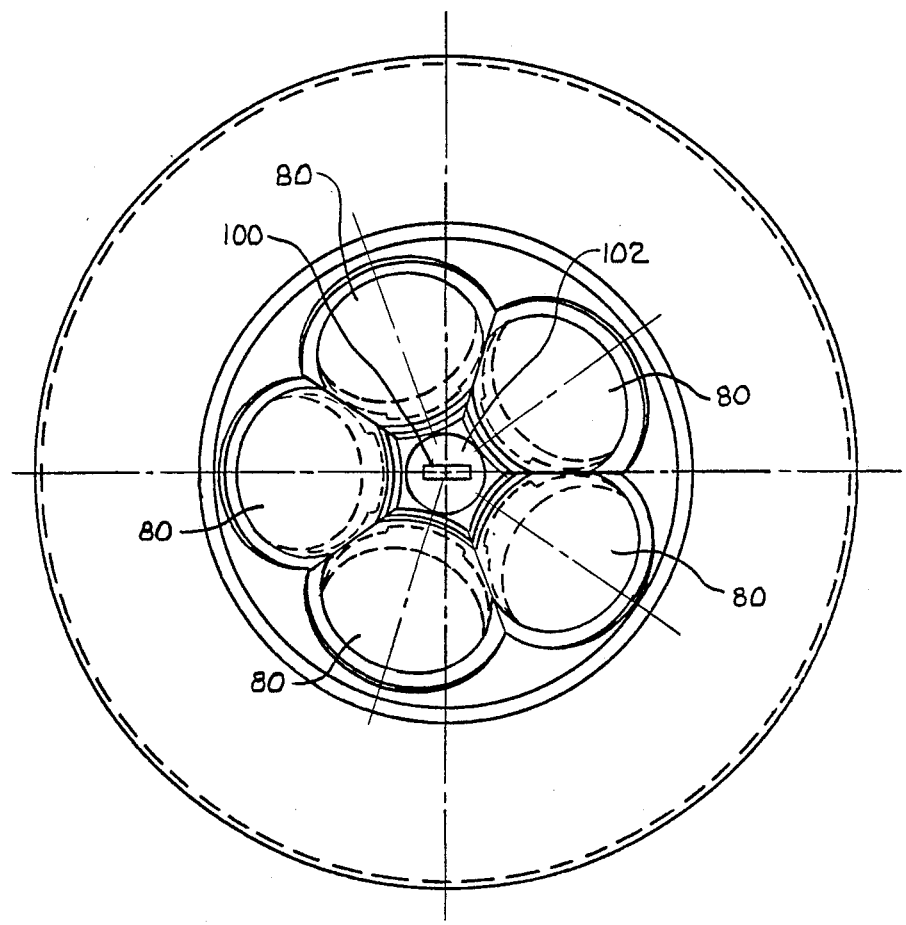
FIG. 7 shows the circumferentially arranged lenses surrounding the radiation source beam.

FIG. 5 illustrates a detailed drawing of a preferred form of sensor 40. A radiating beam 61 is produced by helium cadmium laser 60. The helium-cadmium laser was selected since it produces light in the visible spectrum, is easy to work with, is more stable than UV lasers and produces a higher intensity output that is more efficient than UV. Other lasers producing light at other frequencies could be used but may require a different dye in the penetrant. The laser beam 63 is expanded in beam expander 62 in order to facilitate focusing to a point. The optics necessary for expansion (de-focusing) are well known in the art. The expanded laser beam is reflected by mirror 64 onto mirror 66 from whence it is reflected through focusing lens 68. The lens 68 has a focal length selected to focus the beam onto the plane of surface 11 with a 4 mil diameter. The beam position in one axis is controlled by deflecting off scanning mirror 67. Scanning mirror 67 is comprised of a galvanometer mirror arrangement which generates an electrical signal depending upon its angular position. The scanning mirror 67 may illustratively take the form of a scanning galvanometer unit model G100PD, manufactured by General Scanning, Inc. which generates a voltage signal indicative of mirror angular position. Thus, the beam location can be determined by measuring the voltage from galvanometer 67. Turning briefly to FIG. 7, there is illustrated an end view of sensor 40 showing the circumferential arrangement of lenses 80 for detecting emitted radiation from surface 11. Located centrally of the lenses is a slot-shaped aperture 100 through a lens cover plate 102. The beam is directed through the slot 100 while the plate 102 minimizes reflection of light back onto mirror 67.

When the beam 63 excites any dye on surface 11, the emitted light is focused on fiber optics links 44 by lenses 80. The lenses 80 may be Fresnel lenses. The Fresnel lenses 80 focus detected radiation (reflected light and fluorescing light) from the surface on the fiber optic links 44. Between lenses 80 and links 44, the optical filters 90 remove the blue components as previously described. It might be noted that blue mirrors are used in filter 90 since sharp cut-off filter glass tends to fluoresce under high intensity. The fiber optics links 44 couple the filtered light to photomultiplier tube 46 which converts the light intensity to an electrical signal. One example of a suitable photomultiplier tube is a model R7-12 tube manufactured by the Hamamatsu Corporation.

A feature of sensor 40 in the arrangement of the fiber optic communication link 44 into a narrow rectangular shape similar to slot 100. The lenses 80 are arranged to focus a scan line (see FIG. 4A) onto the receiving ends of the links 44. This arrangement helps to eliminate ghost problems caused by reflected laser light. For example, during operation of the system, laser light may be reflected off the surface of the workpiece to a second location. The second location may contain fluorescent penetrant which will emit light. However, the lenses 80 focus the emitted light from the second location outside the boundaries of the fiber optics links 44 so that the plate 102 blocks reception of such light. Thus, the fiber optics arranged in a narrow rectangular shape increases the signal to noise ratio by preventing secondary emissions from being transmitted to the photomultiplier tube.

Each Fresnel lens focuses light through a similar filter means and onto a separate one of the fiber optics links 44. Each fiber optic link is coupled to the photomultiplier tube 46. In the present invention, the inventors have discovered that five Fresnel lenses each with its own filter 90 and a fiber optic link 44 provides sufficient light detection for dye fluorescing areas at least as small as 4 mils in diameter. For resolution to other values, different numbers of lenses may be utilized.

Figure 6:
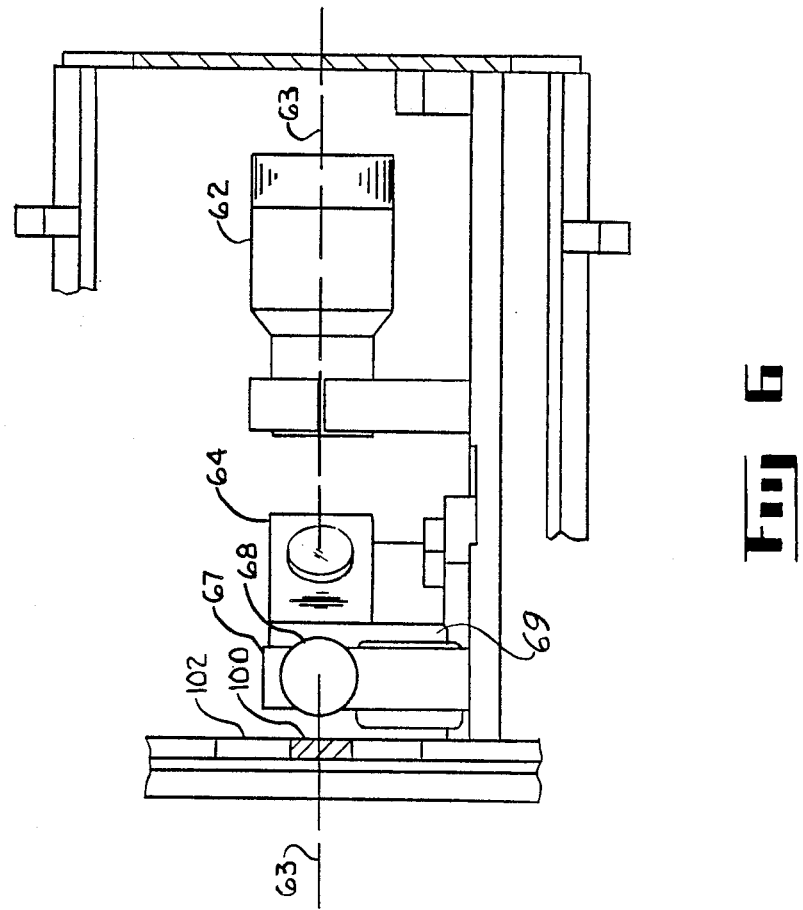
FIG. 6 is a view taken along axis 6—6 in FIG. 5.

Referring to FIG. 6 there is shown sensor 40 taken along the view section 6—6 in FIG. 5. The laser beam 63 is defocused through lens system 62 and reflected by mirror 64. The mirror 66 is not visible in this FIG. 6. However, the focal lens 68 and its holder 69 can be seen. The aperture slit 100 is visible in plate 102.

Referring again to FIG. 7, it will be appreciated that the circumferential arrangement and plurality of Fresnel lenses 80 increases the signal (light) gathering capability of the system. As is evident, the circumferentially arranged Fresnel lenses will receive light emissions from a cone shaped area with the beam focal point being the apex of the cone. The circumferentially arranged lenses also allow the sensor 40 to view the surface 11 from numerous angles. The sensor does not have to be orthogonal to the surface to detect emitted light. The increased light gathering ability of plural lenses allows very minute surface flaws to be detected on the surface of the workpiece. Connecting the sensor 40 to tube 46 by fiber optics links 44 allows movement and positioning of sensor 40 without disturbing tube 46. Such movement may be necessary for inspection of non-planar surfaces.

Thus, there has been shown a fluorescent penetrant inspection sensor comprised of a helium cadmium laser source for generating a directed exciting radiation beam onto a workpiece surface, a plurality of lenses for receiving emitted radiation from the surface, a plurality of filters for removing radiation, a plurality of fiber optic links for transmitting the radiation, and a photomultiplier tube for detecting the emitted radiation intensity. The laser beam is routed to the surface of the workpiece through mirrors and a scanning galvanometer. Manipulation of both the sensor and the workpiece enable the beam to scan the entire surface. A fluorescent dye, excited by the laser beam, emits light which is collected by the plurality of lenses which focus the light through the filters into a fiber optic link which transmits the light to the photomultiplier tube detector. The photomultiplier tube converts the light intensity to electronic signals which are thereafter digitized and sent to a processor. The processor processes the data to correlate emitted light intensity to a location on the surface of the workpiece. The fiber optic bundle allows the sensor to view curved surfaces of the workpiece and the plurality of lenses provides an increased emitted light detection for increasing the signal to noise ratio of the system.

The above described embodiment of the invention is illustrative only, and many modifications thereof may occur to those skilled in the art. Accordingly, this invention is not to be regarded as limited to the embodiments disclosed therein, but is to be interpreted in accordance with the appended claims.

I claim:

1. A nondestructive testing apparatus for detecting flaws on a surface of a workpiece, the workpiece being treated with a substance which fluoresces in the presence of exciting radiation, the substance being trapped in flaws in the workpiece surface, said apparatus comprising:
   a light source for directing a beam of exciting radiation onto the surface of the workpiece;
   detector means for sensing radiation within a predetermined frequency range and generating an electrical signal representative thereof;
   a plurality of lenses positioned for receiving fluorescing radiation emitted from the surface in response to the exciting radiation, said lenses focusing said fluorescing radiation onto said detector means, said plurality of lenses being circumferentially arranged around the directed radiation beam;
   a plurality of light receiving means included in said radiation detector means, each of said lenses focusing radiation on at least one of said light receiving means; a radiation to electrical signal converter; and a plurality of light transmitting means, each of said light transmitting means coupled to one of said light receiving means for coupling said radiation to said converter;
   a light filter located between each of said plurality of lenses and said detector means for blocking reflected exciting radiation;
   processing means responsive to said fluorescing radiation for generating an indication of a flaw; and
   means for effecting movement of said directed beam of exciting radiation for radiating different locations on the workpiece surface, said movement means generating a signal representative of a location of the beam on the workpiece surface, said movement means including an oscillating deflecting mirror positioned to deflect the radiation beam from the light source onto said workpiece surface, said mirror effecting a scanning motion of said radiation beam, said processing means being responsive to said signal for providing data identifying the location of the flaw.

2. The apparatus of claim 1 wherein said beam has a diameter of about four mils at the workpiece surface.

3. The apparatus of claim 1 wherein said light source comprises:
   a laser for producing a radiation beam within a predetermined frequency range;
   a first lens for defocusing the laser beam;
   a first mirror for deflecting the laser beam angularly with respect to its initial axis;
   a second mirror for deflecting the laser beam;
   a second lens for focusing the beam onto the workpiece surface;
   said second mirror being positioned to direct the beam through the second lens and onto the oscillating mirror.

4. A sensor for detecting emitted radiation from a substance being contained in a surface defect of a workpiece, the substance receiving radiation in a first predetermined frequency range and emitting radiation in a second predetermined frequency range, said sensor comprising:
   a radiation source for generating a radiation beam in the first frequency range;
   directing means for directing the radiation beam onto the surface of the workpiece;
   scanning means for producing controlled positioning of the beam on the surface of the workpiece;
   means for receiving light radiation from the workpiece surfaces;

a plurality of lenses arranged circumferentially about the directed radiation beam for receiving emitted radiation in the second frequency range from the surface of the workpiece and focusing the emitted radiation onto the light receiving means;

filter means coupled to said lenses for blocking reflected radiation;

detector means for converting radiation to electrical signals;

light transmission means coupled to said light receiving means for transmitting light to the radiation detector means, said detector means providing an electrical signal representative of the intensity of the emitted radiation, said light receiving means and light transmission means comprising a fiber optics communication link, said light receiving means being arranged in a rectangular shape, such that radiation from the workpiece surface arising remote from the beam location is not focused on said receiving means.

5. The sensor of claim 4 wherein said beam has a diameter of about four mils at the workpiece surface.

6. A method for detecting and locating flaws on the surface of a workpiece using a radiation source for generating a directed laser beam of exciting radiation and a radiation detector responsive to emitted radiation from the surface of the workpiece, said method comprising the steps of:

(a) applying a fluorescent penetrant to the workpiece which seeps into flaws of the workpiece surface, the penetrant being of the type which fluoresces in response to impinging radiation;

(b) orienting the workpiece in the radiation beam for exposure to the radiation beam;

(c) defocusing the laser beam;

(d) refocusing the beam onto the workpiece surface with a diameter of about four mils;

(e) providing a signal representative of beam position on the workpiece surface;

(f) focusing emitted radiation from the penetrant on the radiation detector; and (g) correlating the intensity of emitted radiation with the beam position signal for determining the presence and location of a flaw.

7. The method of claim 6, wherein step (b) of orienting includes the step of:

(f) effecting a scanning movement of the exciting radiation beam.

* * * * *